US012661055B2

(12) United States Patent (10) Patent No.: US 12,661,055 B2
Lindemann et al. (45) Date of Patent: Jun. 23, 2026

(54) MEANS AND METHODS FOR ASSESSING HUNTINGTON'S DISEASE OF THE PRE-MANIFEST STAGE

(71) Applicant: Hoffmann-La Roche Inc., Little Falls, NJ (US)

(72) Inventors: Michael Lindemann, Basel (CH); Florian Lipsmeier, Basel (CH); Cedric André Marie Vincent Geoffrey Simillion, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 923 days.

(21) Appl. No.: 17/772,215

(22) PCT Filed: Nov. 3, 2020

(86) PCT No.: PCT/EP2020/080755
§ 371 (c)(1),
(2) Date: Apr. 27, 2022

(87) PCT Pub. No.: WO2021/089509
PCT Pub. Date: May 14, 2021

(65) Prior Publication Data
US 2022/0401010 A1 Dec. 22, 2022

(30) Foreign Application Priority Data

Nov. 4, 2019 (EP) ..................................... 19206919

(51) Int. Cl.
*A61B 5/00* (2006.01)
*A61B 5/11* (2006.01)
(Continued)

(52) U.S. Cl.
CPC .......... *A61B 5/4082* (2013.01); *A61B 5/1124* (2013.01); *G16H 40/63* (2018.01);
(Continued)

(58) Field of Classification Search
CPC ... A61B 5/4082; A61B 5/1124; A61B 5/1101; A61B 5/1125; A61B 5/7264; G16H 40/63; G16H 50/20; G16H 20/30
See application file for complete search history.

(56) References Cited

U.S. PATENT DOCUMENTS

2005/0187436 A1* 8/2005 Doniger ................... A61B 5/16
128/920
2012/0172682 A1* 7/2012 Linderman ............ A61B 5/389
600/300
(Continued)

FOREIGN PATENT DOCUMENTS

JP      2003-228701 A      8/2003
JP      2013-524879 A      6/2013
(Continued)

OTHER PUBLICATIONS

Caligiuri M, et al. Handwriting Movement Abnormalities in Symptomatic and Premanifest Huntington's Disease. Mov Disord Clin Pract. 2019;6(7):586-592. Published Aug. 16, 2019. doi:10.1002/mdc3.12824 (Year: 2019).*
(Continued)

*Primary Examiner* — Eric F Winakur
*Assistant Examiner* — Sienna C Pyle
(74) *Attorney, Agent, or Firm* — Stinson LLP

(57) ABSTRACT

The present invention relates to the field of diagnostics. Specifically, it relates to a method for assessing Huntington's disease of the pre-manifest stage in a subject comprising the steps of determining at least one performance parameter from a dataset of fine motoric measurements from said subject, comparing the determined at least one performance parameter to a reference, and assessing Huntington's disease of the pre-manifest stage in the subject based on said comparison. Yet, the invention contemplates a device and a system for carrying out the aforementioned methods and the
(Continued)

Figure 1:
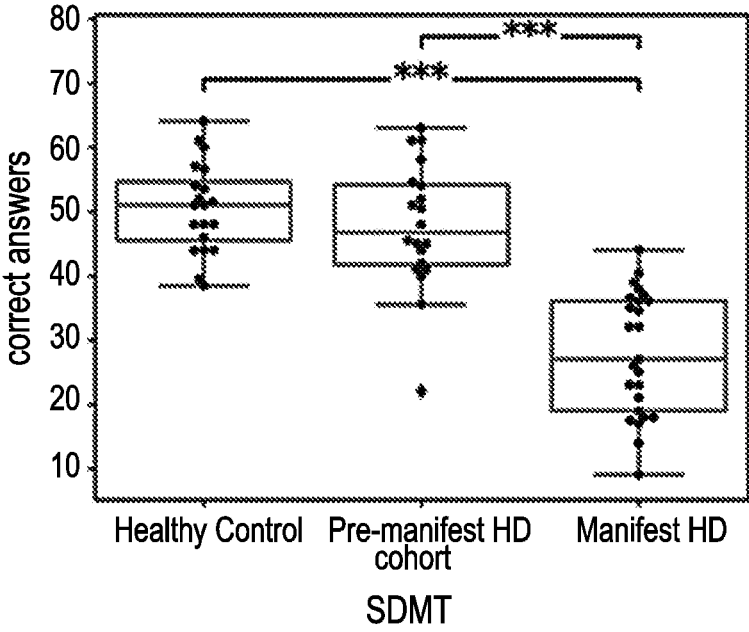
Figure 1:
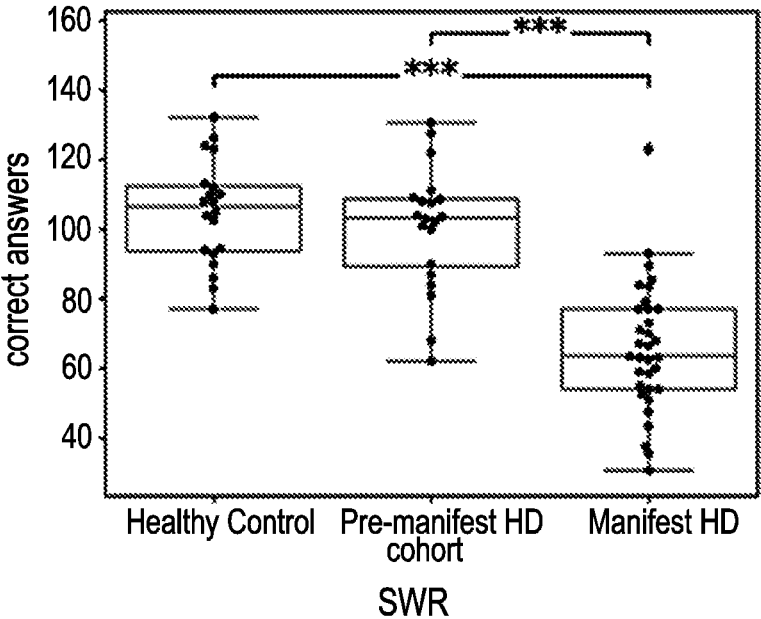
Figure 1:
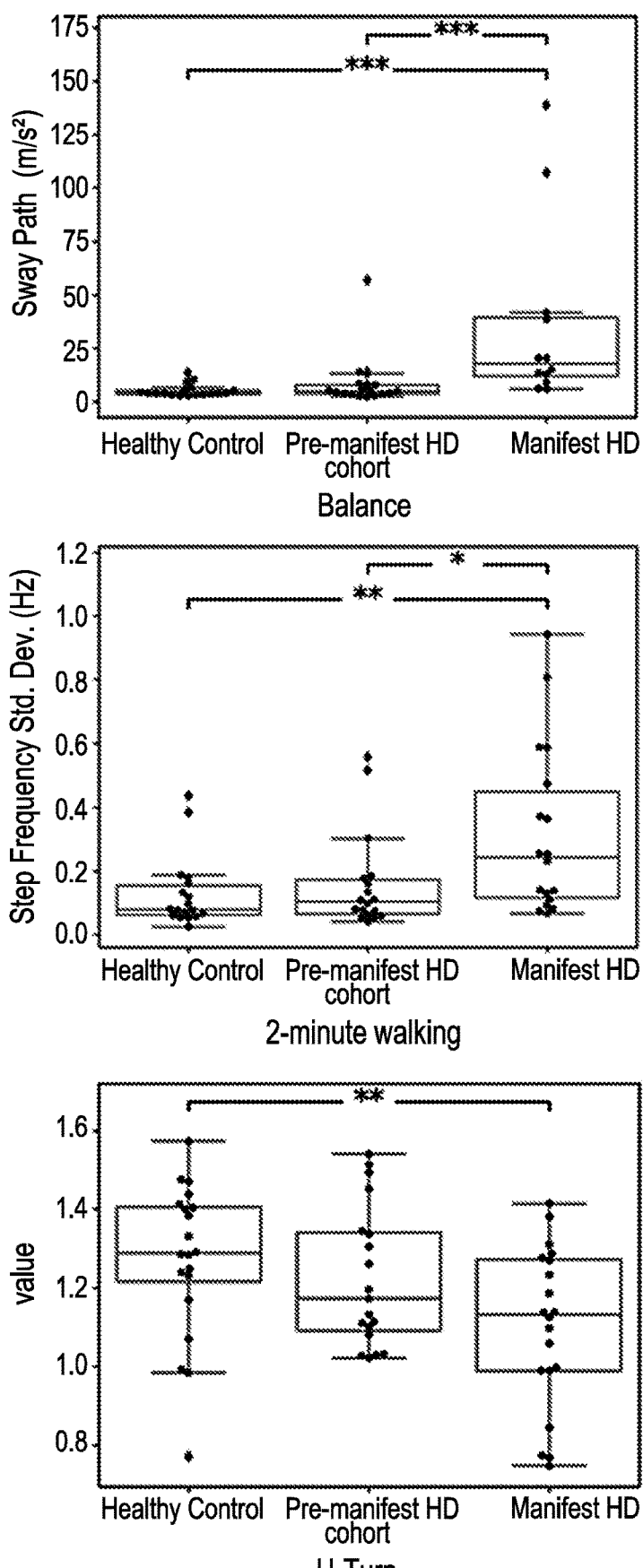
Figure 1:
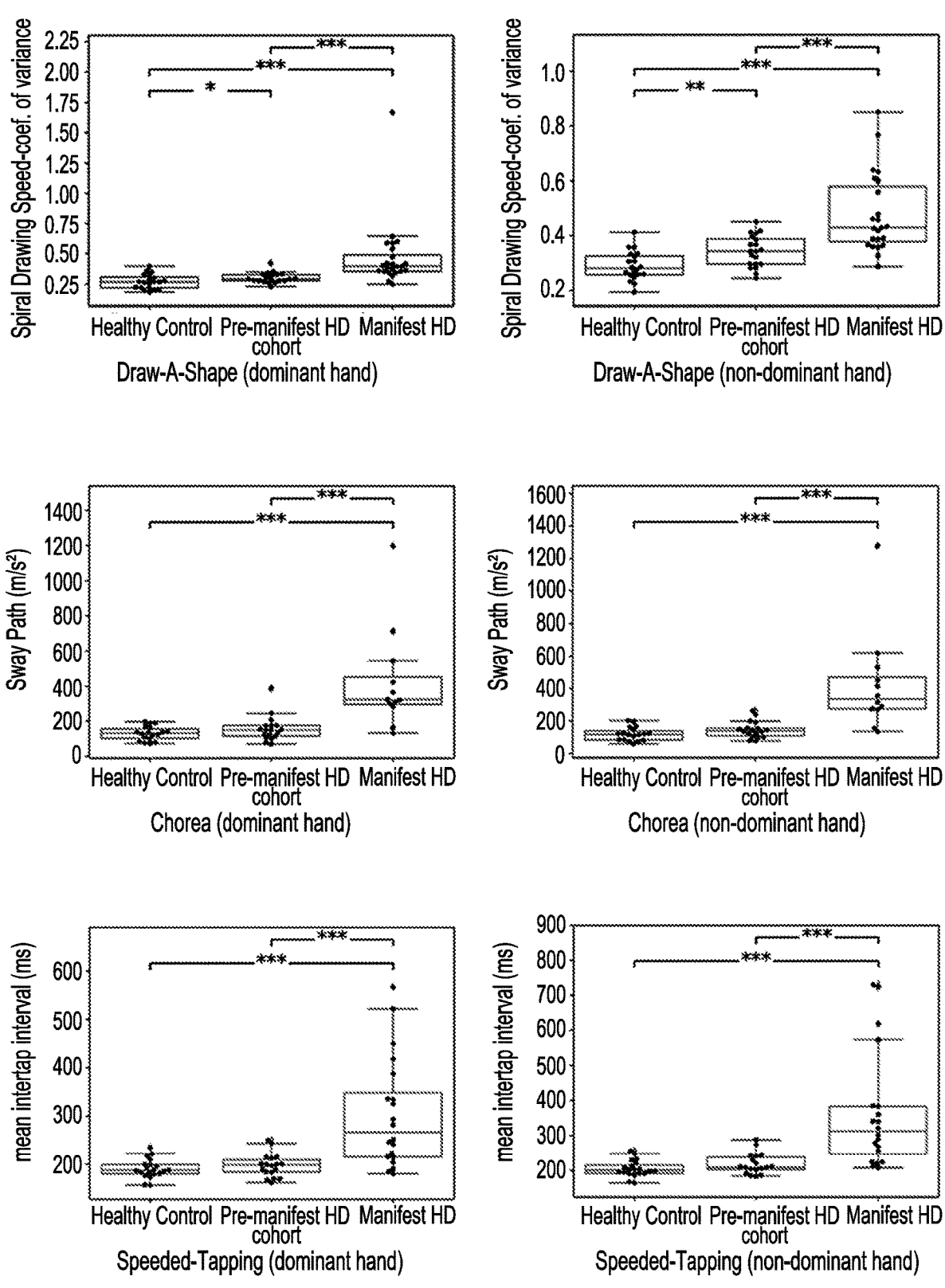

use of such device or system for assessing Huntington's disease of the pre-manifest stage in the subject.

13 Claims, 5 Drawing Sheets

(51) Int. Cl.
| | |
|---|---|
| *G16H 20/30* | (2018.01) |
| *G16H 40/63* | (2018.01) |
| *G16H 50/20* | (2018.01) |

(52) U.S. Cl.
CPC ............ *G16H 50/20* (2018.01); *A61B 5/1101* (2013.01); *G16H 20/30* (2018.01)

(56) References Cited

U.S. PATENT DOCUMENTS

| | | | | |
|---|---|---|---|---|
| 2014/0074180 A1* | 3/2014 | Heldman | ........... | A61N 1/36067 |
| | | | | 607/45 |
| 2014/0336539 A1* | 11/2014 | Torres | .................... | A61B 5/162 |
| | | | | 600/595 |
| 2020/0305789 A1* | 10/2020 | Horne | .................. | A61B 5/4842 |

FOREIGN PATENT DOCUMENTS

| | | |
|---|---|---|
| WO | 2018050763 A1 | 3/2018 |
| WO | 2019081640 A2 | 5/2019 |

OTHER PUBLICATIONS

Paulsen JS, Langbehn DR, Stout JC, et al. Detection of Huntington's disease decades before diagnosis: the Predict-HD study. J Neurol Neurosurg Psychiatry. 2008 (Year: 2008).*

Living with Huntington's Disease—For Better Recuperation—Ver. 2, Report of Research Committee of CNS Degenerative Diseases, Feb. 2017, partial translation of pp. 1-2.

The Huntington Study Group, "Unified Huntington's Disease Rating Scale: Reliability and Consistency," 1996, Movement Disorders, 11(2): pp. 136-142.

Rao et al., "Clinical measurement of mobility and balance impairments in Huntington's disease: Validity and responsiveness," 2009, Gait & Posture. 29 (3): 433-436.

Rao et al., "Coordination of fingertip forces during precision grip in premanifest Huntington's disease," Movement Disorders, 26(5), 2011: pp. 862-869.

Bechtel et al., "Tapping linked to function and structure in premanifest and symptomatic Huntington disease," Neurology, 75(24), 2010: pp. 2150-2160.

* cited by examiner

MEANS AND METHODS FOR ASSESSING HUNTINGTON'S DISEASE OF THE PRE-MANIFEST STAGE

This application is a U.S. national phase application of PCT/EP2020/080755, filed Nov. 3, 2020, which claims priority to EP patent application Ser. No. 19/206,919.3, filed Nov. 4, 2019, both of which are hereby incorporated by reference in their entireties.

The present invention relates to the field of diagnostics. Specifically, it relates to a method for assessing Huntington's disease of the pre-manifest stage in a subject comprising the steps of determining at least one performance parameter from a dataset of fine motoric measurements from said subject, comparing the determined at least one performance parameter to a reference, and assessing Huntington's disease of the pre-manifest stage in the subject based on said comparison. Yet, the invention contemplates a device and a system for carrying out the aforementioned methods and the use of such device or system for assessing Huntington's disease of the pre-manifest stage in the subject.

Huntington's Disease is an inherited neurological disorder accompanied by neuronal cell death in the central nervous system. Most prominently, the basal ganglia are affected by cell death. There are also further areas of the brain involved such as sub stantia nigra, cerebral cortex, hippocampus and the purkinje cells. All regions, typically, play a role in movement and behavioral control.

The disease is caused by genetic mutations in the gene encoding Huntingtin. Huntingtin is a protein involved in various cellular functions and interacts with over 100 other proteins. The mutated Huntingtin appears to be cytotoxic for certain neuronal cell types.

The symptoms of the disease most commonly become noticeable in the mid-age, but can begin at any age from infancy to the elderly. In early stages, symptoms involve subtle changes in personality, cognition, and physical skills. The physical symptoms are usually the first to be noticed, as cognitive and behavioral symptoms are generally not severe enough to be recognized on their own at said early stages.

The most characteristic initial physical symptoms are jerky, random, and uncontrollable movements called chorea. Chorea may be initially exhibited as general restlessness, small unintentionally initiated or uncompleted motions, lack of coordination, or slowed saccadic eye movements. These minor motor abnormalities usually precede more obvious signs of motor dysfunction by at least three years. The clear appearance of symptoms such as rigidity, writhing motions or abnormal posturing appear as the disorder progresses.

Further symptoms of Huntington's disease include physical instability, abnormal facial expression, and difficulties chewing, swallowing, and speaking. Consequently, eating difficulties and sleep disturbances are also accompanying the disease. Cognitive abilities are also impaired in a progressive manner. Impaired are executive functions, cognitive flexibility, abstract thinking, rule acquisition, and proper action/reaction capabilities. In more pronounced stages, memory deficits tend to appear including short-term memory deficits to long-term memory difficulties. Cognitive problems worsen over time and will ultimately turn into dementia. Psychiatric complications accompanying Huntington's disease are anxiety, depression, a reduced display of emotions (blunted affect), egocentrism, aggression, and compulsive behavior, the latter of which can cause or worsen addictions, including alcoholism, gambling, and hyper sexuality.

There is no cure for Huntington's disease. There are supportive measurements in disease management depending on the symptoms to be addressed. Moreover, a number of drugs are used to ameliorate the disease, its progression or the symptoms accompanying it.

The disease can be diagnosed by genetic testing. Moreover, the severity of the disease can be staged according to Unified Huntington's Disease Rating Scale (UHDRS). (The Huntington Group, 1996, Rao 2009) This scale system addresses four components, i.e. the motor function, the cognition, behavior and functional abilities. The motor function assessment includes assessment of ocular pursuit, saccade initiation, saccade velocity, dysarthria, tongue protrusion, maximal dystonia, maximal chorea, retropulsion pull test, finger taps, pronate/supinate hands, luria, rigidity arms, bradykinesia body, gait, and tandem walking and can be summarized as total motor score (TMS). The motoric functions must be investigated and judged by a medical practitioner in a hospital of medical doctor's residency.

Computer-implemented tests for assessing Huntington's disease have been described, inter alia, in WO 2019/081640.

However, diagnostic tools are needed that allow a reliable diagnosis and identification of the Huntington's disease of the pre-manifest stage in patients in order to allow for proper care and/or an accurate treatment.

The technical problem underlying the present invention may be seen in the provision of means and methods complying with the aforementioned needs. The technical problem is solved by the embodiments characterized in the claims and described herein below.

The present invention relates to a method for assessing Huntington's disease of the pre-manifest stage in a subject comprising the steps of:

a) determining at least one performance parameter from a dataset of fine motoric measurements from said subject;

b) comparing the determined at least one performance parameter to a reference; and c) assessing Huntington's disease of the pre-manifest stage in the subject based on said comparison.

The method is, typically, a computer implemented method, i.e. the steps a) to c) are carried out in an automated manner by use of a data processing device. Details are also found herein below and in the accompanying Examples.

In some embodiments, the method may also comprise prior to step (a) the step of obtaining from the subject using a mobile device a dataset of fine motoric measurements from said subject during predetermined activity performed by the subject or during a predetermined time window. However, typically the method is an ex vivo method carried out on an existing dataset of measurements from a subject which does not require any physical interaction with the said subject.

The method as referred to in accordance with the present invention includes a method which essentially consists of the aforementioned steps or a method which may include additional steps.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "particularly", "more particularly", "specifically", "more specifically", "typically", and "more typically" or similar terms are used in conjunction with additional/alternative features, without restricting alternative possibilities. Thus, features introduced by these terms are additional/alternative features and are not intended to restrict the scope of the claims in any way. The invention may, as the skilled person will recognize, be performed by using alternative features. Similarly, features introduced by "in an embodiment of the invention" or similar expressions are intended to be additional/alternative features, without any restriction regarding alternative embodiments of the invention, without any restrictions regarding the scope of the invention and without any restriction regarding the possibility of combining the features introduced in such way with other additional/alternative or non-additional/alternative features of the invention.

The method may be carried out on the mobile device by the subject once the dataset of fine motoric measurements has been acquired. Thus, the mobile device and the device acquiring the dataset may be physically identical, i.e. the same device. Such a mobile device shall have a data acquisition unit which typically comprises means for data acquisition, i.e. means which detect or measure either quantitatively or qualitatively physical and/or chemical parameters and transform them into electronic signals transmitted to the evaluation unit in the mobile device used for carrying out the method according to the invention. The data acquisition unit comprises means for data acquisition, i.e. means which detect or measure either quantitatively or qualitatively physical and/or chemical parameters and transform them into electronic signals transmitted to the device being remote from the mobile device and used for carrying out the method according to the invention. Typically, said means for data acquisition comprise at least one sensor. It will be understood that more than one sensor can be used in the mobile device, i.e. at least two, at least three, at least four, at least five, at least six, at least seven, at least eight, at least nine or at least ten or even more different sensors. Typical sensors used as means for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, sweat analysis sensors and the like. The evaluation unit typically comprises a processor and a database as well as software which is tangibly embedded to said device and, when running on said device, carries out the method of the invention. More typically, such a mobile device may also comprise a user interface, such as a screen, which allows for providing the result of the analysis carried out by the evaluation unit to a user.

Alternatively, it may be carried out on a device being remote with respect to the mobile device that has been used to acquire the said dataset. In this case, the mobile device shall merely comprise means for data acquisition, i.e. means which detect or measure either quantitatively or qualitatively physical and/or chemical parameters and transform them into electronic signals transmitted to the device being remote from the mobile device and used for carrying out the method according to the invention. Typically, said means for data acquisition comprise at least one sensor. It will be understood that more than one sensor can be used in the mobile device, i.e. at least two, at least three, at least four, at least five, at least six, at least seven, at least eight, at least nine or at least ten or even more different sensors. Typical sensors used as means for data acquisition are sensors such as gyroscope, magnetometer, accelerometer, proximity sensors, thermometer, humidity sensors, pedometer, heart rate detectors, fingerprint detectors, touch sensors, voice recorders, light sensors, pressure sensors, location data detectors, cameras, sweat analysis sensors, GPS, and the like. Thus, the mobile device and the device used for carrying out the method of the invention may be physically different devices. In this case, the mobile device may correspond with the device used for carrying out the method of the present invention by any means for data transmission. Such data transmission may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Accordingly, for carrying out the method of the present invention, the only requirement is the presence of a dataset of measurements obtained from a subject using a mobile device. The said dataset may also be transmitted or stored from the acquiring mobile device on a permanent or temporary memory device which subsequently can be used to transfer the data to the device used for carrying out the method of the present invention. The remote device which carries out the method of the invention in this setup typically comprises a processor and a database as well as software which is tangibly embedded to said device and, when running on said device, carries out the method of the invention. More typically, the said device may also comprise a user interface, such as a screen, which allows for providing the result of the analysis carried out by the evaluation unit to a user.

The term "assessing" as used herein refers to assessing whether a subject suffers from Huntington's disease in the pre-manifest stage, or not. Accordingly, assessing as used herein includes diagnosing, staging, classifying and/or predicting Huntington's disease of the pre-manifest stage or recommending therapies against Huntington's disease of the pre-manifest stage. As will be understood by those skilled in the art, such an assessment, although preferred to be, may usually not be correct for 100% of the investigated subjects. The term, however, requires that a statistically significant portion of subjects can be correctly assessed. Whether a portion is statistically significant can be determined without further ado by the person skilled in the art using various well known statistic evaluation tools, e.g., determination of confidence intervals, p-value determination, Student's t-test, Mann-Whitney test, etc. Details may be found in Dowdy and Wearden, Statistics for Research, John Wiley & Sons, New York 1983. Typically envisaged confidence intervals are at least 50%, at least 60%, at least 70%, at least 80%, at least 90%, at least 95%. The p-values are, typically, 0.2, 0.1, 0.05. Thus, the method of the present invention, typically, aids the assessment of Huntington's disease by providing a means for evaluating a dataset of fine motoric measurements.

The term "Huntington's disease (HD)" as used herein relates to an inherited neurological disorder accompanied by neuronal cell death in the central nervous system. Most prominently, the basal ganglia are affected by cell death. There are also further areas of the brain involved such as substantia nigra, cerebral cortex, hippocampus and the purkinje cells. All regions, typically, play a role in movement and behavioral control. The disease is caused by genetic mutations in the gene encoding Huntingtin. Huntingtin is a protein involved in various cellular functions and interacts with over 100 other proteins. The mutated Huntingtin appears to be cytotoxic for certain neuronal cell types. Mutated Huntingtin is characterized by a poly glutamine region caused by a trinucleotide repeat in the Huntingtin gene. A repeat of more than 36 glutamine residues in the poly glutamine region of the protein results in the disease causing Huntingtin protein. Since Huntington's disease is inherited in a dominant autosomal manner, genome testing for CAG repeats in the huntingtin (HTT) alleles is recommended for individuals being genetically at risk, i.e. patients with a corresponding family history of the disease. Moreover, diagnosis of the disease involves DNA analysis but also imaging methods such as CT, MRI, PET or SPECT scanning, in order to determine cerebral atrophy as well as neurological assessment by a medical practitioner.

The symptoms of the disease most commonly become noticeable in the mid-age, but can begin at any age from infancy to the elderly. In early stages, symptoms involve subtle changes in personality, cognition, and physical skills. The physical symptoms are usually the first to be noticed, as cognitive and behavioral symptoms are generally not severe enough to be recognized on their own at said early stages. Almost everyone with Huntington's disease eventually exhibits similar physical symptoms, but the onset, progression and extent of cognitive and behavioral symptoms vary significantly between individuals. The most characteristic initial physical symptoms are jerky, random, and uncontrollable movements called chorea. Chorea may be initially exhibited as general restlessness, small unintentionally initiated or uncompleted motions, lack of coordination, or slowed saccadic eye movements. These minor motor abnormalities usually precede more obvious signs of motor dysfunction by at least three years. The clear appearance of symptoms such as rigidity, writhing motions or abnormal posturing appear as the disorder progresses. These are signs that the system in the brain that is responsible for movement has been affected. Psychomotor functions become increasingly impaired, such that any action that requires muscle control is affected. Common consequences are physical instability, abnormal facial expression, and difficulties chewing, swallowing, and speaking. Consequently, eating difficulties and sleep disturbances are also accompanying the disease. Cognitive abilities are also impaired in a progressive manner. Impaired are executive functions, cognitive flexibility, abstract thinking, rule acquisition, and proper action/reaction capabilities. In more pronounced stages, memory deficits tend to appear including short-term memory deficits to long-term memory difficulties. Cognitive problems worsen over time and will ultimately turn into dementia. Psychiatric complications accompanying Huntington's disease are anxiety, depression, a reduced display of emotions (blunted affect), egocentrism, aggression, and compulsive behavior, the latter of which can cause or worsen addictions, including alcoholism, gambling, and hypersexuality.

There is no cure for Huntington's disease. There are supportive measurements in disease management depending on the symptoms to be addressed. Moreover, a number of drugs are used to ameliorate the disease, its progression or the symptoms accompanying it. Tetrabenazine is approved for treatment of Huntington's disease, include neuroleptics and benzodiazepines are used as drugs that help to reduce chorea, amantadine or ramacemide are still under investigation but have shown preliminary positive results. Hypokinesia and rigidity, especially in juvenile cases, can be treated with antiparkinsonian drugs, and myoclonic hyperkinesia can be treated with valproic acid. Ethyl-eicosapentoic acid was found to enhance the motor symptoms of patients, however, its long term effects need to be revealed.

The disease can be diagnosed by genetic testing. Moreover, the severity of the disease can be staged according to Unified Huntington's Disease Rating Scale (UHDRS). This scale system addresses four components, i.e. the motor function, the cognition, behavior and functional abilities. The motor function assessment includes assessment of ocular pursuit, saccade initiation, saccade velocity, dysarthria, tongue protrusion, maximal dystonia, maximal chorea, retropulsion pull test, finger taps, pronate/supinate hands, luria, rigidity arms, bradykinesia body, gait, and tandem walking and can be summarized as total motor score (TMS). The motoric functions must be investigated and judged by a medical practitioner.

The "pre-manifest stage" of Huntington's disease is a stage were subjects do not exhibit any clinical symptom of Huntington's disease. However, some motoric functions may be weaker than in subjects which do not suffer from Huntington's disease in a pre-manifest stage. Typically, the subject has a TMS of 15 or less, 12 or less, 10 or less, 8 or less, or 5 or less. Moreover, subjects shall be carriers of the HTT genetic mutations (CAG repeats).

The term "fine motoric measurements" refers to accuracy, dexterity and/or speed of fine motoric movements of extremities and, more typically, finger movement accuracy and/or dexterity and/or movement speed. Said measurements of finger movement accuracy and/or dexterity and/or movement speed are carried out during tapping movements and/or drawing movements as described below. The at least one performance parameter can be typically determined from datasets of measurements collected from the subject during carrying out the following activities for fine motoric capabilities. The following tests are typically computer-implemented on a data acquisition device such as a mobile device as specified elsewhere herein.

Tests for Fine Motoric Capabilities: Draw a Shape Test

The mobile device may be adapted for performing or acquiring a data from a further test for distal motor function (so-called "draw a shape test") configured to measure dexterity and distal fine motoric of the fingers. The dataset acquired from such test allow identifying the precision of finger movements, pressure profile and speed profile.

The aim of the "Draw a Shape" test is to assess fine finger control and stroke sequencing. The patients are instructed to hold the mobile device in the untested hand and draw on a touchscreen of the mobile device 6 pre-written alternating shapes of increasing complexity (linear, rectangular, circular, sinusoidal, and spiral; vide infra) with the second finger of the tested hand "as fast and as accurately as possible" within a maximum time of for instance 30 seconds. To draw a shape successfully the patient's finger has to slide continuously on the touchscreen and connect indicated start and end points passing through all indicated check points and keeping within the boundaries of the writing path as much as possible. The patient has maximum two attempts to successfully complete each of the 6 shapes. Test will be alternatingly performed with right and left hand. User will be instructed on daily alternation. The two linear shapes have each a specific number "a" of checkpoints to connect, i.e. "a-1" segments. The square shape has a specific number "b" of checkpoints to connect, i.e. "b-1" segments. The circular shape has a specific number "c" of checkpoints to connect, i.e. "c-1" segments. The eight-shape has a specific number "d" of checkpoints to connect, i.e. "d-1" segments. The spiral shape has a specific number "e" of checkpoints to connect, "e-1" segments. Completing the 6 shapes then implies to draw successfully a total of "(2a+b+c+d+e−6)" segments.

Typical Draw a Shape Test Performance Parameters of Interest:

Based on shape complexity, the linear and square shapes can be associated with a weighting factor (Wf) of 1, circular and sinusoidal shapes a weighting factor of 2, and the spiral shape a weighting factor of 3. A shape which is successfully completed on the second attempt can be associated with a weighting factor of 0.5. These weighting factors are numerical examples which can be changed in the context of the present invention.

1. Shape completion performance scores:
    a. Number of successfully completed shapes (0 to 6) ($\Sigma$Sh) per test
    b. Number of shapes successfully completed at first attempt (0 to 6) ($\Sigma$Sh$_1$)
    c. Number of shapes successfully completed at second attempt (0 to 6) ($\Sigma$Sh$_2$)
    d. Number of failed/uncompleted shapes on all attempts (0 to 12) ($\Sigma$F)
    e. Shape completion score reflecting the number of successfully completed shapes adjusted with weighting factors for different complexity levels for respective shapes (0 to 10) ($\Sigma$[Sh*Wf])
    f. Shape completion score reflecting the number of successfully completed shapes adjusted with weighting factors for different complexity levels for respective shapes and accounting for success at first vs second attempts (0 to 10) ($\Sigma$[Sh$_1$*Wf]+$\Sigma$[Sh$_2$*Wf*0.5])
    g. Shape completion scores as defined in #1e, and #1f may account for speed at test completion if being multiplied by 30/t, where t would represent the time in seconds to complete the test.
    h. Overall and first attempt completion rate for each 6 individual shapes based on multiple testing within a certain period of time: ($\Sigma$Sh$_1$)/($\Sigma$Sh$_1$+$\Sigma$Sh$_2$+$\Sigma$F) and ($\Sigma$Sh$_1$+$\Sigma$Sh$_2$)/($\Sigma$Sh$_1$+$\Sigma$Sh$_2$+$\Sigma$F).
  2. Segment completion and celerity performance scores/measures: (analysis based on best of two attempts [highest number of completed segments] for each shape, if applicable)
    a. Number of successfully completed segments (0 to [2a+b+c+d+e−6]) ($\Sigma$Se) per test
    b. Mean celerity ([C], segments/second) of successfully completed segments: C=$\Sigma$Se/t, where t would represent the time in seconds to complete the test (max 30 seconds)
    c. Segment completion score reflecting the number of successfully completed segments adjusted with weighting factors for different complexity levels for respective shapes ($\Sigma$[Se*Wf])
    d. Speed-adjusted and weighted segment completion score ($\Sigma$[Se*Wf]*30/t), where t would represent the time in seconds to complete the test.

e. Shape-specific number of successfully completed segments for linear and square shapes ($\Sigma$Se$_{LS}$)
    f. Shape-specific number of successfully completed segments for circular and sinusoidal shapes ($\Sigma$Se$_{CS}$)
    g. Shape-specific number of successfully completed segments for spiral shape ($\Sigma$Se$_S$)
    h. Shape-specific mean linear celerity for successfully completed segments performed in linear and square shape testing: C$_L$=$\Sigma$Se$_{LS}$/t, where t would represent the cumulative epoch time in seconds elapsed from starting to finishing points of the corresponding successfully completed segments within these specific shapes.
    i. Shape-specific mean circular celerity for successfully completed segments performed in circular and sinusoidal shape testing: C$_C$=$\Sigma$Se$_{CS}$/t, where t would represent the cumulative epoch time in seconds elapsed from starting to finishing points of the corresponding successfully completed segments within these specific shapes.
    j. Shape-specific mean spiral celerity for successfully completed segments performed in the spiral shape testing: C$_S$=$\Sigma$Se$_S$/t, where t would represent the cumulative epoch time in seconds elapsed from starting to finishing points of the corresponding successfully completed segments within this specific shape.
  3. Drawing precision performance scores/measures: (analysis based on best of two attempts[highest number of completed segments] for each shape, if applicable)
    a. Deviation (Dev) calculated as the sum of overall area under the curve (AUC) measures of integrated surface deviations between the drawn trajectory and the target drawing path from starting to ending checkpoints that were reached for each specific shapes divided by the total cumulative length of the corresponding target path within these shapes (from starting to ending checkpoints that were reached).
    b. Linear deviation (Dev$_L$) calculated as Dev in #3a but specifically from the linear and square shape testing results.
    c. Circular deviation (Dev$_C$) calculated as Dev in #3a but specifically from the circular and sinusoidal shape testing results.
    d. Spiral deviation (Dev$_S$) calculated as Dev in #3a but specifically from the spiral shape testing results.
    e. Shape-specific deviation (Dev$_{1-6}$) calculated as Dev in #3a but from each of the 6 distinct shape testing results separately, only applicable for those shapes where at least 3 segments were successfully completed within the best attempt.
    f. Continuous variable analysis of any other methods of calculating shape-specific or shape-agnostic overall deviation from the target trajectory.
  4.) Pressure profile measurement
    i) Exerted average pressure
    ii) Deviation (Dev) calculated as the standard deviation of pressure More typical performance parameters for fine motoric capabilities in the Draw a Shape test are spiral drawing speed coefficient of variance, circle drawing speed coefficient of variance and/or spiral mean drawing speed. More typically all of these performance parameters may be determined. Further typical performance parameters are also described in the accompanying Examples below.

Tests for Fine Motoric Capabilities: Speed Tapping Test

The aim of the "speed tapping" test is to assess speed of finger movement capabilities. The patients are instructed to hold the mobile device in the untested hand and to tap on the touchscreen of the mobile device with various speed. Speed of tapping may be controlled by showing to the subject a symbol such as a button or circle which need to be touched during the tapping movement.

More typical performance parameters for fine motoric capabilities in the speed tapping test are standard deviation of the time the finger is lifted between to two taps, maximum time the finger is lifted between to two taps, coefficient of variance of the time the finger is lifted between to two taps, coefficient of variance of the distance between two taps, standard deviation of the time the finger touches the screen during a tap, coefficient of variance of the time the finger touches the screen during a tap and/or maximum time the finger touches the screen during a tap. More typically all of these performance parameters may be determined. Further typical performance parameters are also described in the accompanying Examples below.

Further test, which may be carried out together with the aforementioned ones on are those described in WO 2019/ 081640.

The term "subject" as used herein relates to animals and, typically, to mammals. In particular, the subject is a primate and, most typically, a human. The subject in accordance with the present invention shall suffer from or shall be suspected to suffer from Huntington's disease of the pre-manifest stage. As discussed elsewhere herein, several risk factors may determine an increased prevalence for Huntington's disease and subjects being affect by such risk factors may be deemed to be subjects being suspected to suffer from Huntington's disease of the pre-manifest stage.

The term "at least one" means that one or more performance parameter may be determined in accordance with the invention, i.e. at least two, at least three, at least four or even more different performance parameters. Thus, there is no upper limit for the number of different performance parameter which can be determined in accordance with the method of the present invention. Typically, the parameter(s) are selected from dataset of fine motoric measurements and comprise measurements of finger movement accuracy and/ or dexterity and/or movement speed and, more typically, those performance parameters mentioned specifically elsewhere herein. The measurements of finger movement accuracy and/or dexterity and/or movement speed are carried out during tapping movements and/or drawing movements of fingers. Such movements are, more typically, are carried out using a mobile device, such as a smartphone, smartwatch, wearable sensor, portable multimedia device or tablet computer, having implemented a test which requires input from a subject to be tested such that finger movement accuracy and/or dexterity and/or movement speed can be determined. Suitable tests to be implemented on the mobile device are described elsewhere herein.

The term "performance parameter" as used herein refers to a parameter which is indicative for the capability of a subject to carry out a certain activity during the measurement fine motoric activity, such as finger movements. Typically, the performance parameter may be the accuracy or speed with which a fine motoric task can be performed, e.g., finger movements on a screen. For example, the performance parameter may be determined from a dataset of measurements of tapping movements on a screen using a finger. In such a case the speed of tapping may be determined as a performance parameter. Alternatively or in addition, finger movement accuracy and/or speed may be determined as a performance parameter under conditions where the finger movement is a task in a test, such as drawing a certain predefined shape on the screen.

The term "dataset of measurements" refers to the entirety of data which has been acquired by the mobile device from a subject during measurements of fine motoric capabilities from said subject or to a subset of such data. The dataset according to the method of the present invention may be derived from a fine motoric test performed by a subject to be tested. The subject may carry out a computer implemented test for fine motoric capabilities as described elsewhere herein. Further details are found in the accompanying Examples, below, Determining at least one performance parameter can be achieved either by deriving a desired measured value from the dataset as the performance parameter directly. Alternatively, the parameter may integrate one or more measured values from the dataset and, thus, may be a derived from the dataset by mathematical operations such as calculations. Typically, the performance parameter is derived from the dataset by an automated algorithm, e.g., by a computer program which automatically derives the performance parameter from the dataset of measurements when tangibly embedded on a data processing device feed by the said dataset.

The term "reference" as used herein refers to a discriminator which allows for assessing Huntington's disease of the pre-manifest stage based on the determined at least one performance parameter. Such a discriminator may be a value for the performance parameter which is indicative normal (i.e. healthy) subjects or for subjects suffering from Huntington's disease of the pre-manifest stage.

Such a value may be derived from one or more contrast vision parameters of subjects known to suffer from Huntington's disease of the pre-manifest stage. Typically, the average or median of the parameter may be used as a discriminator in such a case. If the determined performance parameter from the subject is identical to the reference or above a threshold derived from the reference, the subject can be identified as suffering from Huntington's disease of the pre-manifest stage in such a case. If the determined performance parameter differs from the reference and, in particular, is below the said threshold, the subject shall be identified as not suffering from Huntington's disease of the pre-manifest stage.

Similarly, a value may be derived from one or more performance parameters of subjects known not to suffer from Huntington's disease of the pre-manifest stage. Typically, the average or median of the parameter may be used as a discriminator in such a case. If the determined performance parameter from the subject is identical to the reference or below a threshold derived from the reference, the subject can be identified as not suffering from Huntington's disease of the pre-manifest stage in such a case. If the determined performance parameter differs from the reference and, in particular, is above the said threshold, the subject shall be identified as suffering from Huntington's disease of the pre-manifest stage.

As an alternative, the reference may be a previously determined performance parameter from a dataset of measurements which has been obtained from the same subject prior to the actual dataset. In such a case, a determined performance parameter determined from the actual dataset which differs with respect to the previously determined parameter shall be indicative for either an improvement or worsening depending on the previous status of the Huntington's disease of the pre-manifest stage. The skilled person knows based on the kind of activity and previous parameter how the said parameter can be used as a reference.

Comparing the determined at least one performance parameter to a reference can be achieved by an automated comparison algorithm implemented on a data processing device such as a computer. Compared to each other are the values of a determined performance parameter and a reference for said determined parameter as specified elsewhere herein in detail. As a result of the comparison, it can be assessed whether the determined performance parameter is identical or differs from or is in a certain relation to the reference (e.g., is larger or lower than the reference). Based on said assessment, the subject can be identified as suffering from Huntington's disease ("rule-in"), or not ("rule-out"). For the assessment, the kind of reference will be taken into account as described elsewhere in connection with suitable references according to the invention.

Moreover, by determining the degree of difference between a determined performance parameter and a reference, a quantitative assessment of Huntington's disease of the pre-manifest stage in a subject shall be possible. It is to be understood that an improvement, worsening or unchanged condition can be determined by comparing an actually determined performance parameter to an earlier determined one used as a reference. Based on quantitative differences in the value of the said performance parameter the improvement, worsening or unchanged condition can be determined and, optionally, also quantified. If other references, such as references from subjects suffering from Huntington's disease of the pre-manifest stage are used, it will be understood that the quantitative differences are meaningful if a certain stage of impairment can be allocated to the reference collective. Relative to this stage of impairment, worsening, improvement or unchanged condition can be determined in such a case and, optionally, also quantified.

The assessment made by the method of the present invention is indicated to the subject or to another person, such as a medical practitioner. Typically, this is achieved by displaying the diagnosis on a display of the mobile device or the evaluation device. Alternatively, a recommendation for a therapy, such as a drug treatment, or for a certain life style, e.g. rehabilitation measures, is provided automatically to the subject or other person. To this end, the established assessment is compared to recommendations allocated to different assessments in a database. Once the established assessment matches one of the stored and allocated assessments, a suitable recommendation can be identified due to the allocation of the recommendation to the stored assessment matching the established assessment. Accordingly, it is, typically, envisaged that the recommendations and assessments are present in form of a relational database. However, other arrangements which allow for the identification of suitable recommendations are also possible and known to the skilled artisan.

Moreover, the one or more performance parameter may also be stored on the mobile device or indicated to the subject, typically, in real time. The stored performance parameters may be assembled into a time course or similar evaluation measures. Such evaluated performance parameters may be provided to the subject as a feedback for the course of Huntington's disease investigated in accordance with the method of the invention. Typically, such a feedback can be provided in electronic format on a suitable display of the mobile device and can be linked to a recommendation for a therapy as specified above or rehabilitation measures.

Further, the evaluated performance parameters may also be provided to medical practitioners in doctor's offices or hospitals as well as to other health care providers, such as, developers of diagnostic tests or drug developers in the context of clinical trials, health insurance providers or other stakeholders of the public or private health care system.

Typically, the method of the present invention for assessing Huntington's disease of the pre-manifest stage in a subject may be carried out as follows:

First, at least one performance parameter is determined from an existing dataset of fine motoric measurements from said subject using a mobile device. Said dataset may be transmitted from the mobile device to an evaluating device, such as a computer, or may be processed in the mobile device in order to derive the at least one performance parameter from the dataset.

Second, the determined at least one performance parameter is compared to a reference by, e.g., using a computer-implemented comparison algorithm carried out by the data processor of the mobile device or by the evaluating device, e.g., the computer. The result of the comparison is assessed with respect to the reference used in the comparison and based on the said comparison Huntington's disease of the pre-manifest stage in the subject will be assessed, e.g., the subject will be identified as suffering from Huntington's disease of the pre-manifest stage, or not.

Third, the said assessment, e.g., the identification of the subject as suffering from Huntington's disease of the pre-manifest stage, or not, is indicated to the subject or to another person, such as a medical practitioner, on a suitable display such as a screen connected or implemented in the mobile device or the evaluation device.

Alternatively, a recommendation for a therapy, such as a drug treatment, or for a certain life style, is provided automatically to the subject or other person. To this end, the established assessment is compared to recommendations allocated to different assessments in a database. Once the established assessment matches one of the stored and allocated assessments, a suitable recommendation can be identified due to the allocation of the recommendation to the stored assessment matching the established assessment.

Yet as an alternative or in addition, the at least one performance parameter underlying the assessment will be stored on the mobile device. Typically, it shall be evaluated together with other stored performance parameters by suitable evaluation tools, such as time course assembling algorithms, implemented on the mobile device which can assist electronically rehabilitation or therapy recommendation as specified elsewhere herein.

The invention, in light of the above, also specifically contemplates a method for assessing Huntington's disease of the pre-manifest stage in a subject comprising the steps of:
  a) obtaining from said subject using a mobile device a dataset of fine motoric measurements;
  b) determining at least one performance parameter determined from said dataset obtained from said subject using a mobile device;
  c) comparing the determined at least one performance parameter to a reference; and
  d) assessing Huntington's disease of the pre-manifest stage in the subject based on the comparison carried out in step c).

Advantageously, it has been found in the studies underlying the present invention that performance parameters obtained from dataset of fine motoric measurements from said subject can be used as digital biomarkers for assessing Huntington's disease of the pre-manifest stage. It has been found in accordance with the present invention that fine motoric measurements and, in particular, finger movement accuracy and/or dexterity and/or movement speed, such as finger movement accuracy and/or dexterity and/or movement speed are carried out during tapping movements and/or drawing movements of fingers, allows for identifying patients suffering from Huntington's disease of the pre-manifest stage. Such measurements can be conveniently be carried out using computer-implemented test, e.g., tests implemented on a mobile device. Thanks to the use of a mobile device, the patient may carry out the test at any time and in any place. There is no need for consultation of a medical practitioner in a doctor's office or hospital ambulance for performing the measurement. Thanks to the present invention, the life conditions of Huntington's disease patients, in particular, at early stages, can be adjusted more precisely to the actual disease status due to the use of actual determined performance parameters by the method of the invention. Thereby, drug treatments can be selected that are more efficient or dosage regimens can be adapted to the current status of the patient. It is to be understood that the method of the invention is, typically, a data evaluation method which requires an existing dataset of activity measurements from a subject.

Accordingly, the method of the present invention may be used for:

assessing the disease condition;
    monitoring patients, in particular, in a real life, daily situation and on large scale;
    supporting patients with life style and/or therapy recommendations;
    investigating drug efficacy, e.g. also during clinical trials;
    facilitating and/or aiding therapeutic decision making;
    supporting hospital managements;
    supporting rehabilitation measure management;
    improving the disease condition as a rehabilitation instrument stimulating higher density cognitive, motoric and walking activity
    supporting health insurances assessments and management; and/or
    supporting decisions in public health management.

The definitions and explanations of the terms made above apply mutatis mutandis for the following embodiments except as specified otherwise.

In an embodiment of the method of the invention, the said of fine motoric measurements comprise measurements of finger movement accuracy and/or dexterity and/or movement speed. More typically, said measurements of finger movement accuracy and/or dexterity and/or movement speed are carried out during tapping movements and/or drawing movements of fingers.

In an embodiment of the method of the invention, said measurements are carried out using a mobile device. More typically, said mobile device is comprised in a smartphone, smartwatch, wearable sensor, portable multimedia device or tablet computer.

In an embodiment of the method of the present invention, said method is computer-implemented.

In yet an embodiment of the method of the present invention, the reference is at least one performance parameter from a dataset of fine motoric measurements from said subject wherein said dataset has been obtained prior to the dataset of step a).

In an embodiment of the method of the present invention, the reference is at least one performance parameter from a dataset of fine motoric measurements from at least one subject known to suffer from Huntington's disease of the pre-manifest stage. More typically, at least one performance parameter being essentially identical to the reference is indicative for a subject suffering from Huntington's disease of the pre-manifest stage.

In an embodiment of the method of the present invention, the reference is at least one performance parameter from a dataset of fine motoric measurements from at least one subject known not to suffer from Huntington's disease of the pre-manifest stage. More typically, at least one performance parameter which differs from the reference is indicative for a subject suffering from Huntington's disease of the pre-manifest stage.

In yet an embodiment of the method of the present invention, said assessing Huntington's disease of the pre-manifest stage comprises diagnosing and/or predicting Huntington's disease of the pre-manifest stage or recommending therapies against Huntington's disease of the pre-manifest stage.

The present invention also encompasses a method for determining efficacy of a therapy against Huntington's disease of the pre-manifest stage comprising the steps of the method of the invention (i.e. the method for assessing Huntington's disease of the pre-manifest stage) and the further step of determining a therapy response if improvement of the Huntington's disease of the pre-manifest stage occurs in the subject upon therapy or determining a failure of response if worsening of Huntington's disease of the pre-manifest stage occurs in the subject upon therapy or if Huntington's disease of the pre-manifest stage remains unchanged.

The term "a therapy against Huntington's disease of the pre-manifest stage" as used herein refers to all kinds of medical treatments, including drug-based therapies, respiratory support and the like. The term also encompasses, life-style recommendations and rehabilitation measures. Typically, the method encompasses recommendation of a drug-based therapy and, in particular, a therapy with a drug known to be useful for the treatment of Huntington's disease of the pre-manifest stage. Such drug may be tetrabenazine, neuroleptics, benzodiazepines, amantadine, ramacemide, antiparkinsonian drugs, valproic acid or ethyl-eicosapentoic acid. Moreover, the aforementioned method may comprise in yet an embodiment the additional step of applying the recommended therapy to the subject.

Moreover, encompassed in accordance with the present invention is a method for determining efficacy of a therapy against Huntington's disease of the pre-manifest stage comprising the steps of the aforementioned method of the invention (i.e. the method for assessing Huntington's disease of the pre-manifest stage) and the further step of determining a therapy response if improvement of Huntington's disease of the pre-manifest stage occurs in the subject upon therapy or determining a failure of response if worsening of Huntington's disease of the pre-manifest stage occurs in the subject upon therapy or if Huntington's disease of the pre-manifest stage remains unchanged.

The term "improvement" as referred to in accordance with the present invention relates to any improvement of the overall disease condition or of individual symptoms thereof and, in particular, the contrast vision capabilities. Likewise, a "worsening" means any worsening of the overall disease condition or individual symptoms thereof and, in particular, the contrast vision capabilities. Since, Huntington's disease as a progressing disease is associated typically with a worsening of the overall disease condition and symptoms thereof, the worsening referred to in connection with the aforementioned method is an unexpected or untypical worsening which goes beyond the normal course of the disease. Unchanged Huntington's disease of the pre-manifest stage means that the overall disease condition and the symptoms accompanying it are within the normal course of the disease.

Moreover, the present invention pertains to a method of monitoring Huntington's disease of the pre-manifest stage in a subject comprising determining whether said disease improves, worsens or remains unchanged in a subject by carrying out the steps of the method of the invention (i.e. the method of assessing Huntington's disease of the pre-manifest stage) at least two times during a predefined monitoring period.

The present invention relates to a mobile device comprising a processor, at least one sensor and a database as well as software which is tangibly embedded to said device and, when running on said device, carries out the method of the invention.

The term "mobile device" as used herein refers to any portable device which comprises at least a sensor and data-recording equipment suitable for obtaining the dataset of the above measurements. This may also require a data processor and storage unit as well as a display for electronically simulating a test for fine motoric capabilities on the mobile device. The data processor may comprise a Central Processing Unit (CPU) and/or one or more Graphics Processing Units (GPUs) and/or one or more Application Specific Integrated Circuits (ASICs) and/or one or more Tensor Processing Units (TPUs) and/or one or more field-programmable gate arrays (FPGAs) or the like. Moreover, from the activity of the subject data shall be recorded and compiled to a dataset which is to be evaluated by the method of the present invention either on the mobile device itself or on a second device. Depending on the specific setup envisaged, it may be necessary that the mobile device comprises data transmission equipment in order to transfer the acquired dataset from the mobile device to further device. Particular well suited as mobile devices according to the present invention are smartphones, portable multimedia devices or tablet computers. Alternatively, portable sensors with data recording and processing equipment may be used. Further, depending on the kind of activity test to be performed, the mobile device shall be adapted to display instructions for the subject regarding the activity to be carried out for the test. Particular envisaged activities to be carried out by the subject are described elsewhere herein and encompass the tests for fine motoric capabilities as described in this specification.

The present invention contemplates a system comprising a mobile device comprising at least one sensor and a remote device comprising a processor and a database as well as software which is tangibly embedded to said device and, when running on said device, carries out the method of the invention, wherein said mobile device and said remote device are operatively linked to each other.

Under "operatively linked to each other" it is to be understood that the devices are connect as to allow data transfer from one device to the other device. Typically, it is envisaged that at least the mobile device which acquires data from the subject is connect to the remote device carrying out the steps of the methods of the invention such that the acquired data can be transmitted for processing to the remote device. However, the remote device may also transmit data to the mobile device such as signals controlling or supervising its proper function. The connection between the mobile device and the remote device may be achieved by a permanent or temporary physical connection, such as coaxial, fiber, fiber-optic or twisted-pair, 10 BASE-T cables. Alternatively, it may be achieved by a temporary or permanent wireless connection using, e.g., radio waves, such as Wi-Fi, LTE, LTE-advanced or Bluetooth. Further details may be found elsewhere in this specification. For data acquisition, the mobile device may comprise a user interface such as screen or other equipment for data acquisition. Typically, the activity measurements can be performed on a screen comprised by a mobile device, wherein it will be understood that the said screen may have different sizes including, e.g., a 5.1 inch screen.

Yet, the invention relates to the use of the mobile device or the system of the invention for assessing Huntington's disease in a subject using at least one performance parameter from a dataset of measurements of fine motoric measurements from said subject.

The present invention also contemplates the use of the mobile device or the system according to the present invention for monitoring patients, in particular, in a real life, daily situation and on large scale. Encompassed by the present invention is furthermore the use of the mobile device or the system according to the present invention for supporting patients with life style and/or therapy recommendations. Yet, it will be understood that the present invention contemplates the use of the mobile device or the system according to the present invention for investigating drug safety and efficacy, e.g. also during clinical trials. Further, the present invention contemplates the use of the mobile device or the system according to the present invention for facilitating and/or aiding therapeutic decision making. Furthermore, the present invention provides for the use of the mobile device or the system according to the present invention for improving the disease condition as a rehabilitation instrument, and for supporting hospital management, rehabilitation measure management, health insurances assessments and management and/or supporting decisions in public health management.

The present invention also, in principle, contemplates a computer program, computer program product or computer readable storage medium having tangibly embedded said computer program, wherein the computer program comprises instructions when run on a data processing device or computer carry out the method of the present invention as specified above. Specifically, the present disclosure further encompasses:

A computer or computer network comprising at least one processor, wherein the processor is adapted to perform the method according to one of the embodiments described in this description, a computer loadable data structure that is adapted to perform the method according to one of the embodiments described in this description while the data structure is being executed on a computer, a computer script, wherein the computer program is adapted to perform the method according to one of the embodiments described in this description while the program is being executed on a computer, a computer program comprising program means for performing the method according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform the method according to one of the embodiments described in this description after having been loaded into a main and/or working storage of a computer or of a computer network, a computer program product having program code means, wherein the program code means can be stored or are stored on a storage medium, for performing the method according to one of the embodiments described in this description, if the program code means are executed on a computer or on a computer network, a data stream signal, typically encrypted, comprising a dataset of measurements of fine motoric measurements obtained from the subject using a mobile, and a data stream signal, typically encrypted, comprising the at least one performance parameter derived from the dataset of measurements of fine motoric measurements obtained from the subject using a mobile.

The present invention, further, relates to a method for determining at least one performance parameter from a dataset of measurements of fine motoric measurements from said subject using a mobile device a) deriving at least one performance parameter from a dataset of measurements of fine motoric measurements from said subject using a mobile device; and b) comparing the determined at least one performance parameter to a reference, wherein, typically, said at least one performance parameter can aid assessment of Huntington's disease of the pre-manifest stage in said subject.

In the following, further particular embodiments of the invention are listed:

Embodiment 1. A method for assessing Huntington's disease of the pre-manifest stage in a subject comprising the steps of:

a) determining at least one performance parameter from a dataset of fine motoric measurements from said subject;

b) comparing the determined at least one performance parameter to a reference; and c) assessing Huntington's disease of the pre-manifest stage in the subject based on said comparison.

Embodiment 2. The method of embodiment 1, wherein the said of fine motoric measurements comprise measurements of finger movement accuracy and/or dexterity and/or movement speed.

Embodiment 3. The method of embodiment 2, wherein said measurements of finger movement accuracy and/or dexterity and/or movement speed are carried out during tapping movements and/or drawing movements of fingers.

Embodiment 4. The method of any one of embodiments 1 to 3, wherein said measurements are carried out using a mobile device.

Embodiment 5. The method of embodiment 4, wherein said mobile device is comprised in a smartphone, smartwatch, wearable sensor, portable multimedia device or tablet computer.

Embodiment 6. The method of any one of embodiments 1 to 5, wherein said method is computer-implemented.

Embodiment 7. The method of any one of embodiments 1 to 6, wherein the reference is at least one performance parameter from a dataset of fine motoric measurements from said subject wherein said dataset has been obtained prior to the dataset of step a).

Embodiment 8. The method of any one of embodiments 1 to 6, wherein the reference is at least one performance parameter from a dataset of fine motoric measurements from at least one subject known to suffer from Huntington's disease of the pre-manifest stage.

Embodiment 9. The method of embodiment 8, wherein at least one performance parameter being essentially identical to the reference is indicative for a subject suffering from Huntington's disease of the pre-manifest stage.

Embodiment 10. The method of any one of embodiments 1 to 6, wherein the reference is at least one performance parameter from a dataset of fine motoric measurements from at least one subject known not to suffer from Huntington's disease of the pre-manifest stage.

Embodiment 11. The method of embodiment 10, wherein at least one performance parameter which differs from the reference is indicative for a subject suffering from Huntington's disease of the pre-manifest stage.

Embodiment 12. The method of any one of embodiments 1 to 11, wherein said assessing Huntington's disease comprises diagnosing and/or predicting Huntington's disease of the pre-manifest stage or recommending therapies against Huntington's disease of the pre-manifest stage.

Embodiment 13. A mobile device comprising a processor, at least one sensor and a database as well as software which is tangibly embedded to said device and, when running on said device, carries out the method of any one of embodiments 1 to 12.

Embodiment 14. A system comprising a mobile device comprising at least one sensor and a remote device comprising a processor and a database as well as software which is tangibly embedded to said device and, when running on said device, carries out the method of any one of embodiments 1 to 12, wherein said mobile device and said remote device are operatively linked to each other.

Embodiment 15. Use of the mobile device according to embodiment 13 or the system of embodiment 14 for assessing Huntington's disease of the pre-manifest stage in a subject using at least one performance parameter from a dataset of measurements of fine motoric measurements from said subject.

All references cited throughout this specification are herewith incorporated by reference with respect to their entire disclosure content and with respect to the specific disclosure contents mentioned in the specification.

FIGURES

Figure 2:
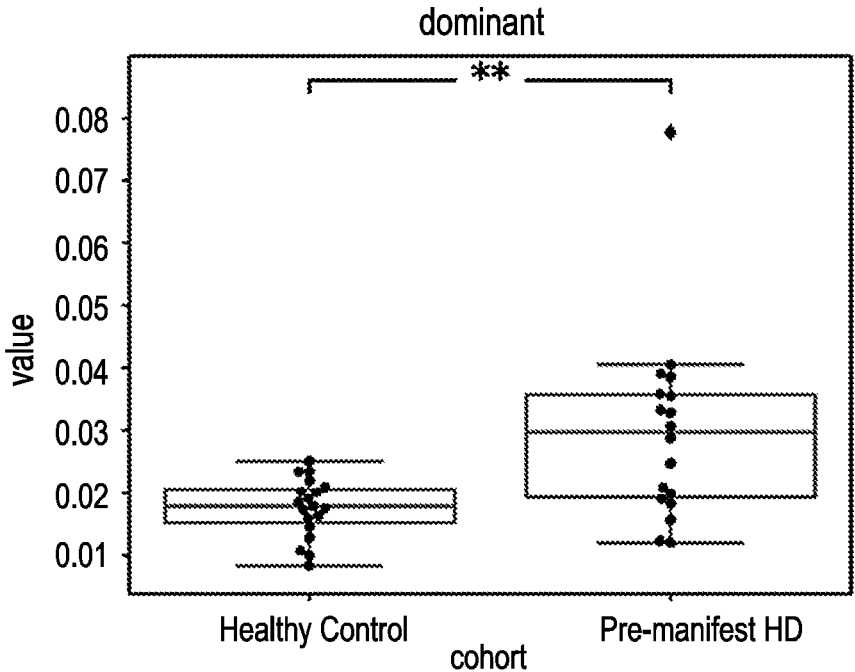
Figure 2:
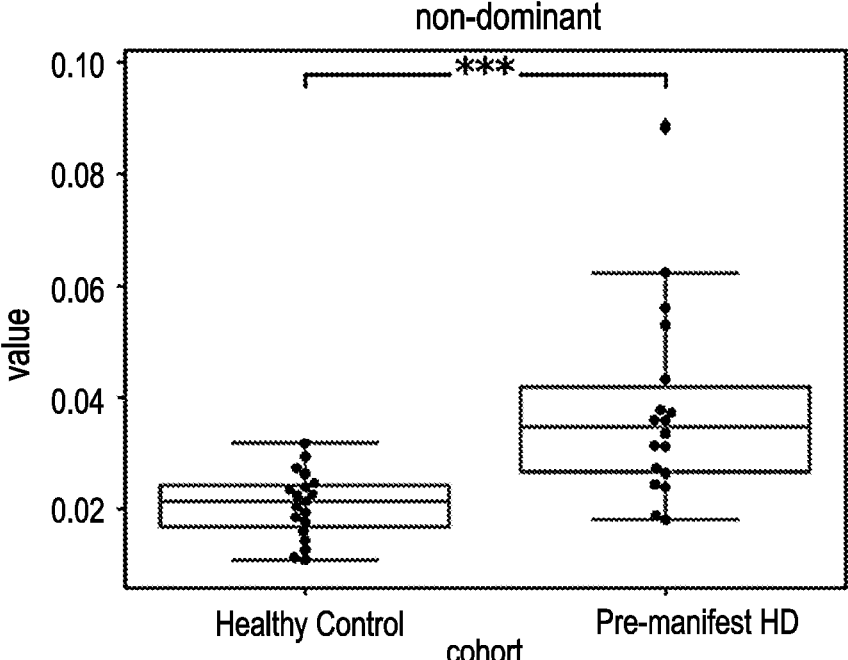

FIGS. 1A-1C: Boxplots comparing the pre-defined features of each mobile device implemented test between the cohorts. Legend: *: $p < 0.05$; : $p < 0.01$; *: $p < 0.001$. (FIG. 1A) Cognitive tests SDMT and SWR, (FIG. 1B) Stability and Gait Tests Balance, 2-minute walking, U-turn (FIG. 1C) Upper-Body Motion Tests Draw a Shape, Chorea and speeded tapping. "Dominant" refers to the dominantly used had, "non-dominant" refers to the non-dominantly used hand FIGS. 2A & 2B: Exploratory analysis of features discriminating the pre-manifest and healthy control cohorts. Legend: *: $p < 0.05$; : $p < 0.01$; *: $p < 0.001$. Shown are features from handed tests which had a $p < 0.01$ for at least one hand and $p < 0.05$ for both hands. The up-time standard deviation feature from the Speeded Tapping test is defined as the standard deviation of the time where the finger was lifted off the screen between consecutive taps; $p = 0.002$ (dominant hand); $p < 0.001$ (non-dominant hand).

Figure 3:
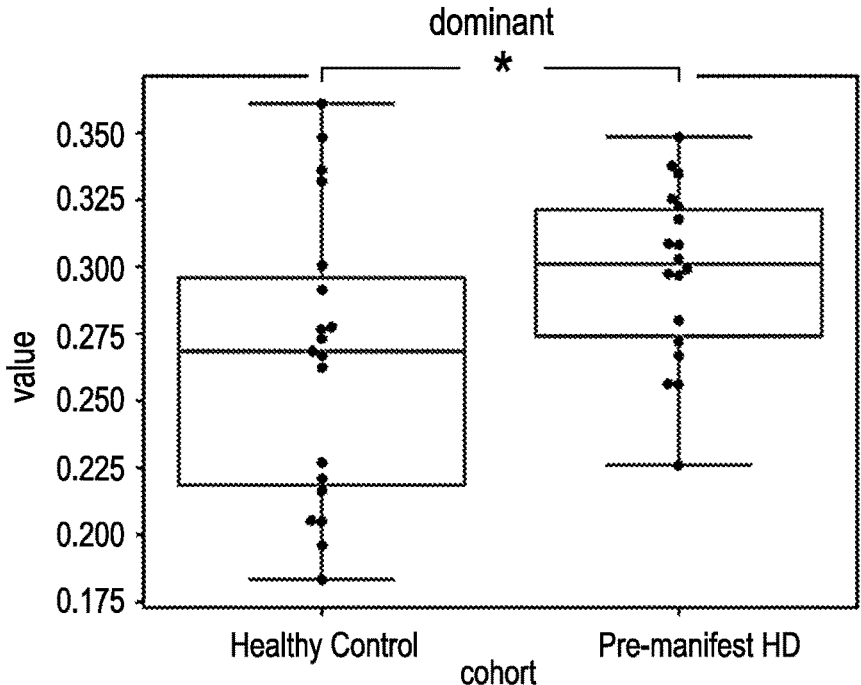
Figure 3:
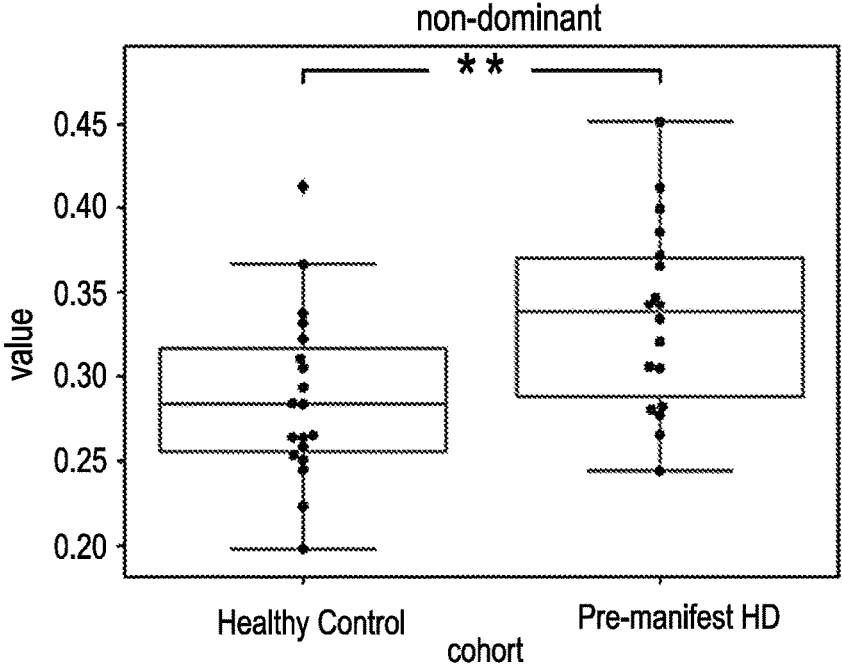

FIGS. 3A & 3B: Exploratory analysis of features discriminating the pre-manifest and healthy control cohorts. Legend: *: $p<0.05$; : $p<0.01$; *: $p<0.001$. Shown are features from handed tests which had a $p<0.01$ for at least one hand and $p<0.05$ for both hands. The Draw a Shape test feature was the same as the coefficient of variance for the spiral drawing speed; $p=0.04$ (dominant hand); $p=0.007$ (non-dominant hand).

EXAMPLES

The following Examples merely illustrate the invention. Whatsoever, they shall not be construed in a way as to limit the scope of the invention.

Example 1: Identification of Novel Features that Discriminate Between Healthy Controls and Pre-Manifest Subjects Study A smartphone application comprising seven active tests (Symbol Digit Modalities Test [SDMT], Stroop Word Reading test [SWRT], Speeded tapping, Chorea, Balance, U-turn, 2-minute walk) and continuous passive monitoring was deployed in an observational study (Digital-HD) of participants with pre-manifest Huntington's disease (HD), manifest HD and healthy controls (HC).

Presented here are results from 79 participants enrolled at time of data cut-off. Predefined active test measurements were aggregated over Weeks 5 and 6 post-screening to minimize practice effects.

This 1-year study aimed to enroll 80 participants (manifest HD: 40, pre-manifest HD: 20, HC: 20). Data were captured from continuous passive monitoring and daily active tests. Passive monitoring involves wearing a smartwatch and carrying a GPS-enabled smartphone, both containing tri-axial accelerometers and gyroscopes. Active tests measure motor and non-motor manifestations of HD, and include questions about motor tasks, cognitive tests, QoL and mood.

Demographic details of the patients are summarized in Table 1, below.

TABLE 1

| | HC | Pre-manifest HD | Manifest HD | Total |
|---|---|---|---|---|
| N | 20 | 20 | 39 | 79 |
| Age, mean (standard deviation [SD]), years | 47.8 (14.2) | 44.4 (10.0) | 56.2 (11.2) | 51.1 (12.7) |
| Female, % | 35.0 | 50.0 | 46.2 | 44.3 |
| Right-hand dominance, % | 85.0 | 100.0 | 74.4 | 83.5 |
| Total Functional Capacity, mean (SD) | 13 (0.0) | 12.9 (0.3) | 10.6 (2.2) | 11.8 (2.0) |
| Total Motor Score, mean (SD) | 1.4 (2.5) | 4.9 (3.9) | 32.9 (16.8) | 17.8 (19.2) |

Participants were trained on active tests during an on-site equipment issue visit (EIV) and performed these tests at home upon prompting.

During the EIV, participants underwent clinical assessments using the Unified HD Rating Scale motor, cognitive and functional subscales, as well as the Timed-up-and-go test and selected items from the Berg Balance Scale alongside a Kinect sensor.

Encrypted phone data were securely transferred via the internet and analysed to extract clinically meaningful measurements for group discrimination and correlation with clinical parameters.

Feature differences between the groups were calculated using the Mann-Whitney test. Correlations with in-clinic counterparts were calculated using Spearman's correlation coefficient.

Results

The SDMT and SWR test showed excellent correlation with their in-clinic counterparts. The Chorea test show good correlation with the UHDRS Maximal Chorea Upper Limb item. All 8 pre-defined features had significant differences between the Manifest and Healthy Control Cohorts with all $p<0.001$ apart from the gait tests (U-Turn: $p=0.009$; 2-minute walking: $p=0.004$) (see FIG. 1). Results are also shown in Table 2, below.

TABLE 2

| test | feature | description | | | |
|---|---|---|---|---|---|
| SPEEDED-TAPPING | uptime_std | standard deviation of the time the finger is lifted between to two taps | 0.001059054 | 0.000288768 | 0.000553011 |
| SPEEDED-TAPPING | longgapcntmad | | 0.002600484 | 0.000451095 | 0.001083082 |
| SPEEDED-TAPPING | uptime_max | maximum time the finger is lifted between to two taps | 0.003149447 | 0.000403984 | 0.001127975 |
| SPEEDED-TAPPING | uptime_cv | coefficient of variance of the time the finger is lifted between to two taps | 0.001059054 | 0.00159178 | 0.001298376 |
| SPEEDED-TAPPING | down_dt_std | | 0.002362109 | 0.000859704 | 0.001425032 |
| SPEEDED-TAPPING | down_dt_max | | 0.002863746 | 0.001439337 | 0.002030245 |
| SPEEDED-TAPPING | down_dt_cv | | 0.003149447 | 0.001942154 | 0.002473199 |
| DRAW-A-SHAPE | SPIRAL_sp_cov | SPIRAL drawing speed coefficient of variance | 0.016064013 | 0.002448697 | 0.006271834 |
| SPEEDED-TAPPING | nexttapdist_cv | coefficient of variance of the distance between two taps | 0.003800152 | 0.014058605 | 0.00730923 |
| DRAW-A-SHAPE | SQUARE_overShoot_mean | | 0.026547517 | 0.002238179 | 0.007708314 |
| SPEEDED-TAPPING | downtime_std | standard devation of the time the finger touches the screen during a tap | 0.005480406 | 0.014058605 | 0.008777635 |
| DRAW-A-SHAPE | CIRCLE_sp_cov | CIRCLE drawing speed coefficient of variance | 0.026547517 | 0.00292502 | 0.008812038 |

TABLE 2-continued

| test | feature | description | | | |
|------|---------|-------------|---|---|---|
| SPEEDED-TAPPING | downtime__cv | coefficient of variance of the time the finger touches the screen during a tap | 0.00926984 | 0.010090761 | 0.009671594 |
| SPEEDED-TAPPING | downtime__max | maximum time the finger touches the screen during a tap | 0.012955226 | 0.026291395 | 0.018455649 |
| DRAW-A-SHAPE | CIRCLE__acc__celerity | | 0.05829058 | 0.006830256 | 0.019953435 |
| DRAW-A-SHAPE | CIRCLE__celerity | | 0.05829058 | 0.006830256 | 0.019953435 |
| SPEEDED-TAPPING | tapmovecnt__std | | 0.020911079 | 0.019344679 | 0.020112636 |
| SPEEDED-TAPPING | tapmovecnt__max | | 0.014048096 | 0.03401407 | 0.021859389 |
| SPEEDED-TAPPING | tapmovecnt__cv | | 0.032828498 | 0.016516759 | 0.023285626 |
| DRAW-A-SHAPE | OVERALL__mean__celerity | | 0.08835202 | 0.006830256 | 0.024565563 |
| DRAW-A-SHAPE | SPIRAL__mag__error__time | | 0.05146206 | 0.011881032 | 0.02472696 |
| DRAW-A-SHAPE | SPIRAL__sp__mean | SPIRAL mean drawing speed | 0.048307143 | 0.012824421 | 0.024889981 |
| SPEEDED-TAPPING | tapposchange__max | | 0.026291395 | 0.026291395 | 0.026291395 |
| SPEEDED-TAPPING | downtime__min | | 0.011919855 | 0.059324888 | 0.02659218 |
| DRAW-A-SHAPE | SPIRAL__error__time | | 0.045316297 | 0.016064013 | 0.026980763 |
| DRAW-A-SHAPE | SPIRAL__MerrorValue | | 0.051462076 | 0.016064013 | 0.028752173 |
| SPEEDED-TAPPING | tapposchange__std | | 0.032828498 | 0.026291395 | 0.029378683 |
| DRAW-A-SHAPE | SQUARE__celerity | | 0.065855484 | 0.01491205 | 0.031337521 |
| DRAW-A-SHAPE | SQUARE__acc__celerity | | 0.065855484 | 0.01491205 | 0.031337521 |
| SPEEDED-TAPPING | down__dt__p95 | | 0.079410626 | 0.012955226 | 0.032074642 |
| DRAW-A-SHAPE | LINE__TOP__TO__BOTTOM__err__sd | | 0.019857262 | 0.052533903 | 0.032298289 |
| DRAW-A-SHAPE | SPIRAL__hausD__t | | 0.048307143 | 0.026547517 | 0.035811097 |
| DRAW-A-SHAPE | SPIRAL__celerity | | 0.034866372 | 0.039801146 | 0.037252135 |
| DRAW-A-SHAPE | SPIRAL__acc__celerity | | 0.034866372 | 0.039801146 | 0.037252135 |
| SPEEDED-TAPPING | touch__x__std__h1 | | 0.037921338 | 0.037921338 | 0.037921338 |
| DRAW-A-SHAPE | CIRCLE__mag__error__time | | 0.074211716 | 0.02475803 | 0.042864157 |
| SPEEDED-TAPPING | tapposchange__mean | | 0.046811892 | 0.040710278 | 0.043654612 |
| DRAW-A-SHAPE | SPIRAL__err__sum | | 0.074211716 | 0.030463803 | 0.047547567 |
| SPEEDED-TAPPING | nexttapdist__std | | 0.061337166 | 0.037921338 | 0.048228491 |
| DRAW-A-SHAPE | SPIRAL__aDS__apen | | 0.045316297 | 0.054787666 | 0.049827444 |
| SPEEDED-TAPPING | nexttapdist__max | | 0.040710278 | 0.061337166 | 0.049970522 |
| SPEEDED-TAPPING | tapposchange__median | | 0.079410626 | 0.040710278 | 0.056857969 |
| DRAW-A-SHAPE | SQUARE__mag__error__time | | 0.08835202 | 0.037264273 | 0.057379211 |
| DRAW-A-SHAPE | FIGURE__8__mag__error__time | | 0.078703997 | 0.04248308 | 0.057823768 |
| DRAW-A-SHAPE | CIRCLE__aDS__apen | | 0.08835202 | 0.04248308 | 0.061265536 |
| DRAW-A-SHAPE | FIGURE__8__aDS__apen | | 0.098931599 | 0.054787666 | 0.073622221 |
| SPEEDED-TAPPING | nexttapdist__mean | | 0.095631733 | 0.074529135 | 0.084423636 |
| CHOREA | DIST | | 0.083415083 | 0.098931599 | 0.090842653 |
| CHOREA | AREA | | 0.083415083 | 0.098931599 | 0.090842653 |

2 candidate features (see FIGS. 2 and 3) where identified that showed promise in discriminating the pre-manifest and healthy control cohorts using speeded tapping and Draw a Shape tests.

CITED REFERENCES

The Huntington Group, 1996, Movement Disorders, 11(2): 136
Rao 2009, Gait Posture. 29 (3): 433-6
WO 2019/081640

The invention claimed is:

1. A method for assessing Huntington's disease of the pre-manifest stage in a subject comprising the steps of:
   a) obtaining from said subject using a mobile device a dataset of fine motoric measurements;
   b) determining at least one performance parameter from the dataset of fine motoric measurements from said subject, wherein the at least one performance parameter is derived from the dataset by an automated algorithm implemented on a data processing device;
   c) comparing by an automated comparison algorithm implemented on the data processing device the determined at least one performance parameter to a reference; and
   d) assessing Huntington's disease of the pre-manifest stage in the subject based on said comparison;
   wherein the fine motoric measurements are measurements of finger movement accuracy, dexterity, or speed, and wherein the fine motoric measurements are carried out by a speed tapping test using the mobile device; and
   wherein the one or more performance parameters for fine motoric capabilities in the speed tapping test are maximum time the finger is lifted between two taps, coefficient of variance of the time the finger is lifted between two taps, coefficient of variance of the distance between two taps, standard deviation of the time the finger touches during a tap, coefficient of variance of the time the finger touches during a tap, and/or maximum time the finger touches during a tap.

2. The method of claim 1, wherein said mobile device is comprised of a smartphone, smartwatch, wearable sensor, portable multimedia device or tablet computer.

3. The method of claim 1, wherein the reference is at least one performance parameter from a dataset of fine motoric measurements from said subject, wherein said dataset has been obtained prior to the dataset of step a).

4. The method of claim 1, wherein the reference is at least one performance parameter from a dataset of fine motoric measurements from at least one subject known to suffer from Huntington's disease of the pre-manifest stage.

5. The method of claim 4, wherein at least one performance parameter being identical to the reference is indicative for a subject suffering from Huntington's disease of the pre-manifest stage.

6. The method of claim 1, wherein the reference is at least one performance parameter from a dataset of fine motoric measurements from at least one subject known not to suffer from Huntington's disease of the pre-manifest stage.

7. The method of claim 6, wherein at least one performance parameter which differs from the reference is indicative for a subject suffering from Huntington's disease of the pre-manifest stage.

8. The method of claim 1, wherein said assessing Huntington's disease of the pre-manifest stage comprises diagnosing or predicting Huntington's disease of the pre-manifest stage.

9. The method of claim 8, wherein said assessing Huntington's disease of the pre-manifest stage further comprises recommending therapies against Huntington's disease of the pre-manifest stage.

10. A mobile device comprising a processor, at least one sensor and a database as well as software which is tangibly embedded to said device and, when running on said device, carries out the method of claim 1.

11. The mobile device of claim 10, wherein the mobile device further comprises data transmission equipment.

12. A system comprising a mobile device comprising at least one sensor and a remote device comprising a processor and a database as well as software which is tangibly embedded to said mobile device and, when running on said mobile device, carries out the method of claim 1, wherein said mobile device and said remote device are operatively linked to each other.

13. The system of claim 12, wherein the mobile device further comprises data transmission equipment and, when running said software on said mobile device, transfers the acquired dataset of fine motoric measurements from the mobile device to the remote device.

* * * * *